(12) United States Patent
Parikh et al.

(10) Patent No.: US 11,007,297 B2
(45) Date of Patent: May 18, 2021

(54) PROCESS FOR MAKING ALIGNED OR TWISTED ELECTROSPUN FIBERS

(71) Applicant: The Johns Hopkins University, Baltimore, MD (US)

(72) Inventors: Kunal S. Parikh, Reynoldsburg, OH (US); Himat Patel, Baltimore, MD (US); Justin Hanes, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 206 days.

(21) Appl. No.: 16/083,774

(22) PCT Filed: Mar. 13, 2017

(86) PCT No.: PCT/US2017/022036
§ 371 (c)(1),
(2) Date: Sep. 10, 2018

(87) PCT Pub. No.: WO2017/156521
PCT Pub. Date: Sep. 14, 2017

(65) Prior Publication Data
US 2019/0071796 A1   Mar. 7, 2019

Related U.S. Application Data

(60) Provisional application No. 62/307,096, filed on Mar. 11, 2016, provisional application No. 62/307,230, filed on Mar. 11, 2016.

(51) Int. Cl.
*D02G 1/02* (2006.01)
*D01D 7/00* (2006.01)
(Continued)

(52) U.S. Cl.
CPC ...... *A61L 17/005* (2013.01); *A61B 17/06166* (2013.01); *A61K 31/5383* (2013.01);
(Continued)

(58) Field of Classification Search
CPC .. D01D 5/0007; D01D 5/0015; D01D 5/0023; D01D 5/003; D01D 5/0038;
(Continued)

(56) References Cited

U.S. PATENT DOCUMENTS 6,743,273 B2   6/2004   Chung
6,753,454 B1   6/2004   Smith
(Continued)

FOREIGN PATENT DOCUMENTS

JP   2008138316   6/2008
WO   2007090102   8/2007
(Continued)

OTHER PUBLICATIONS

Bhardwaj, "Electrospinning: A fascinating fiber fabrication technique", Biotechnol. Adv., 28:325-47 (2010).
(Continued)

*Primary Examiner* — Leo B Tentoni
(74) *Attorney, Agent, or Firm* — Pabst Patent Group LLP

(57) ABSTRACT

A system for forming twisted or aligned electrospun fibers has been developed. The collector for the electrospun fibers is capable of rotation. In some instances, fibers are formed between two collectors, at least one of which rotates to twist the fibers into a multifilament bundle with increased strength. In a second embodiment, a cylindrical collector rotates, and charged polymer jet uniformly coats the surface of the collector. When a drum collector rotates at a high speed, electrospun fibers align and form an array. Optionally, different active agents can be included in the electrospinning solutions to form fiber constructs with different strengths
(Continued)

and controlled release profiles, providing a reproducible method to generate complexed structures based on electrospun fibers and controlled drug delivery profiles.

19 Claims, 9 Drawing Sheets

(51) Int. Cl.
| | |
|---|---|
| *A61L 17/00* | (2006.01) |
| *A61L 17/10* | (2006.01) |
| *A61L 17/12* | (2006.01) |
| *D01D 5/00* | (2006.01) |
| *D01F 1/10* | (2006.01) |
| *D01H 7/02* | (2006.01) |
| *A61L 31/06* | (2006.01) |
| *A61L 31/14* | (2006.01) |
| *A61B 17/06* | (2006.01) |
| *A61K 31/5383* | (2006.01) |
| *D04C 1/06* | (2006.01) |

(52) U.S. Cl.
CPC ............. *A61L 17/105* (2013.01); *A61L 17/12* (2013.01); *A61L 31/06* (2013.01); *A61L 31/148* (2013.01); *D01D 5/003* (2013.01); *D01D 5/0007* (2013.01); *D01D 5/0015* (2013.01); *D01D 5/0023* (2013.01); *D01D 5/0038* (2013.01); *D01D 5/0046* (2013.01); *D01D 5/0076* (2013.01); *D01D 5/0084* (2013.01); *D01F 1/10* (2013.01); *D01F 1/103* (2013.01); *D01H 7/02* (2013.01); *D04C 1/06* (2013.01); *A61L 2300/216* (2013.01); *A61L 2300/402* (2013.01); *A61L 2300/41* (2013.01); *A61L 2300/416* (2013.01); *A61L 2400/12* (2013.01); *D10B 2331/04* (2013.01); *D10B 2331/041* (2013.01); *D10B 2401/12* (2013.01); *D10B 2509/04* (2013.01); *D10B 2509/06* (2013.01)

(58) Field of Classification Search
CPC .. D01D 5/0046; D01D 5/0076; D01D 5/0084; D01D 7/00; D02G 1/02; D10B 2509/04; D10B 2509/06
USPC .................................. 264/171.1, 211.12, 465
See application file for complete search history.

(56) References Cited

U.S. PATENT DOCUMENTS

| | | | | |
|---|---|---|---|---|
| 6,821,479 | B1 | 11/2004 | Smith | |
| 2011/0180951 | A1* | 7/2011 | Teo | ........................ D01D 5/0046 |
| | | | | 264/109 |
| 2013/0071463 | A1* | 3/2013 | Palasis | ...................... A61K 9/70 |
| | | | | 424/423 |
| 2013/0115456 | A1* | 5/2013 | Wagner | ................ D01D 5/0007 |
| | | | | 264/465 X |
| 2014/0079759 | A1* | 3/2014 | Patel | ..................... D01D 5/0076 |
| | | | | 424/443 |
| 2014/0271795 | A1 | 9/2014 | Phaneuf | |

FOREIGN PATENT DOCUMENTS

| | | |
|---|---|---|
| WO | 2009101472 | 8/2009 |
| WO | 2011017698 | 2/2011 |
| WO | 2016192697 | 12/2016 |

OTHER PUBLICATIONS

Dabirian, et al., "Conformal coating of yarns and wired with electrospun nanofibers", Polymer Engineering Science, 1724-1732 (2012).
Leach, et al., "Electrospinning fundamentals: optimizing solution and apparatus parameters", J Vis Exp., (47):2494 (2011).
Li, et al., "Electrospinning nanofibers as uniaxially aligned arrays and layer by layer stacked films", Adv. Mater., 16:1151-70 (2004).
Park, "Electrospinning and its applications", Adv. Nat. Sci. Nanosci. Nanotechnol., Apr. 30, 2002, 5 pages, (2010).
Pistner, et al., "Poly(L-lactide): a long-term degradation study in vivo. Part III. Analytical characterization", Biomaterials, 14: 291-8 (1993).
Sahay, et al., "DesignModifications in Electrospinning Setup for Advanced Applications", Journal of Nanomaterials, pp. 1-17. (2011).
Tonin, "Nanofibers", (ISBN 978-953-7619-86-2, 450 pages, Publisher: InTech, Chapters published Feb. 1, 2010.
Zheng, et al., "Aligned Nanofiber arrays and twisted nanofiber ropes via electrospinning with two frames collector", Advanced Materials Research, 690-693:523-526 (2013).
International Search Report PCT/US2017/022036, dated Jun. 9, 2017.

* cited by examiner

PROCESS FOR MAKING ALIGNED OR TWISTED ELECTROSPUN FIBERS

CROSS-REFERENCE TO RELATED APPLICATIONS

This application is a National Phase application under 35 U.S.C. 371 of PCT/US2017/022036, filed Mar. 13, 2017, which claims benefit of and priority to U.S. Provisional Application Nos. 62/307,096 and 62/307,230, both filed on Mar. 11, 2016, which are hereby incorporated herein by reference in their entirety.

FIELD OF THE INVENTION

The present invention relates generally to medical devices, and more particularly, to a process and apparatus for making parallel, twisted fibers.

BACKGROUND OF THE INVENTION

Electrospinning is a simple and versatile technique first introduced in the early 1900's that employs electric forces to elongate and reduce the diameter of a viscoelastic polymer jet, allowing for the formation of solid fibers ranging from nanometers to microns in diameter (Li, D. & Xia, Y. *Adv. Mater.*, 16, 1151-1170 (2004); Bhardwaj, N. & Kundu, S. C., *Biotechnol. Adv.*, 28, 325-47 (2010)). To date, more than 200 polymers have been electrospun for applications ranging from tissue engineering and drug delivery to textiles, filtration, and sensors (Park, J.-S., *Adv. Nat. Sci. Nanosci. Nanotechnol.*, 1, 043002 (2011)). A traditional electrospinning setup includes a grounded collector, high-voltage power source, and spinneret (connected to a syringe containing a polymer solution released at a controlled rate). Application of high voltage forms a Taylor cone and leads to the ejection of an electrified polymer jet due to the newly created electric field and electrostatic repulsions. As the jet moves towards the grounded collector, solvent evaporates and the jet elongates, allowing for the formation of thin, polymeric fibers (Li, D. & Xia, Y. *Adv. Mater.*, 16, 1151-1170 (2004)).

Within the last fifteen years, the field of electrospinning has progressed significantly, and this simple process can now be found in labs and in companies across the country and around the world. A number of parameters affect the electrospinning process including polymer, solvent, polymer:solvent ratio, flow rate, voltage, distance to collector, collector type and speed, and needle size (Sahay, R., Thavasi, V. & Ramakrishna, S., *J. Nanomater.* (2011); Claudio Tonin, A. A. A. V. and C. V. Nanofibers. (ISBN 978-953-7619-86-2, 450 pages, Publisher: InTech, Chapters published Feb. 1, 2010). Typical electrospinning setups do not have precise control of each of the parameters that affect the process, and also do not allow for simple interchange of collector types. While several modifications have been made to the needle, spinneret, and spraying process to allow for different fibers and conformations, there has been little innovation in collector types or the resulting fibers.

Therefore, it is an object of the present invention to provide a highly controlled method of making twisted micro- and nano-fibers in an electrospinning system.

It is also an object of the present invention to provide a system for electrospinning that is capable of twisting fibers.

It is yet another object of the present invention to provide a system and method to coat devices and fibers with electrospun fibers, as well as to manufacture devices in whole or in part with electrospun fibers

SUMMARY OF THE INVENTION

A system and a method for forming and twisting electrospun fibers have been developed. The electrospinning system includes an electrospinning needle or nozzle, one or two collectors, where charged polymer jet deposits between two parallel collectors, or on the surface of one cylindrical (e.g., drum) collector that is suspended. At least one of the collectors is connected to a motor and capable of rotation, such that the fibers are twisted between the two collectors, or, in the configuration with a drum collector, the collector is rotated for uniform coverage by electrospun fibers.

Polymer solutions can optionally contain an agent such as a therapeutic, prophylactic or diagnostic agent dispersed, mixed, encapsulated in nanoparticles, or conjugated therein.

The electrospun fibers can be nano-fibers, micro-fibers, or a mixture thereof. When fibers are formed between two collectors, the rotation of one collector relative to the other (e.g., the other collector is stationary) results in twisting of fibers, forming a multifilament bundle whose strength is much greater than untwisted fibers. The rotation is generally at a speed between about 100 and about 4,000 rpm. As more rotation leads to more twists of the fibers, the overall diameter of the twisted multifilament generally decreases, and the tensile strength of the twisted multifilament generally increases. The multifilament bundle can have an overall diameter between 5 µm and 1 mm, preferably between 10 µm and 500 µm, and more preferably between 20 µm and 50 µm. The multifilament bundle has considerable tensile strength, despite the small diameter, and therefore can be used in clinical applications such as sutures.

In preferred embodiments, the multifilaments formed from twisting electrospun fibers are optimized for desired tensile strength by selection of the composition, and variations in the number of twists of the fibers, the diameter of the overall multifilament, the molecular weight and chemical composition of the polymer forming the fibers, the loading concentration for electrospinning, as well as the loading amount and chemical composition of agent, if any. In some embodiments, up to 20 wt % active agents can be included in the electrospinning solution without compromising the strength of multifilaments less than 30 µm. Twisting fibers containing different agents in the same or different fibers, and/or in coatings on the fibers, allows for controlled, sustained release of multiple agents in combination.

In other embodiments where a drum, a disc, or another cylindrical collector is used, there is a speed threshold of rotation, above which electrospun fibers are aligned and below which the fibers are randomly positioned on the drum collector. This speed threshold is related to the composition of the polymer solution, the distance between the electrospinning needle/nozzle to the collector, the voltage applied, and the curvature of the cylindrical collector. Generally, aligned fibers form when the rotation of the drum collector is greater than 1,000 rpm.

In another embodiment, devices of various geometries are attached to one or both collectors, and rotated, such that electrospun fibers coat uniformly thereon. A template such as a thread, wire or tube can be attached to the collectors, and the layer of fibers formed around the template can be used as a stent, a tube, or a vessel. The device can also be kept still during the rotation process and after the fibers have been formed the collector can be rotated to twist the fibers uniformly onto the device.

Generally, the two collectors define a plane, and the axis of the electrospinning needle or nozzle is perpendicular or substantially perpendicular to this plane. Alternatively, the axis of the drum collector is perpendicular or substantially perpendicular to the axis defined by the needle or nozzle. This can be varied so that the needle or nozzle is at an angle that is 90°, 85°, 80°, 75°, 70°, 65°, 60°, 55°, 50°, 45°, 40°, 35°, 30°, or other non-parallel angle, with respect to the plane or axis defined by the collectors.

Adaptors for one or both collectors have been developed where a cylindrical rod or a drill chuck can be attached to and connected to a motor shaft via the adaptor.

The system is scalable as the distance between the collectors or between the needle and the collectors can be varied. With a controlled speed of dispensing the charged polymer solution, and a motorized stage to control the position of the needle, this system allows for consistent and reproducible production of twisted multifilament bundles, sheets made from aligned electrospun fibers, coatings on any device of interest, and hollow, tubular structures.

DETAILED DESCRIPTION OF THE INVENTION

I. Definitions

Figure 1A:
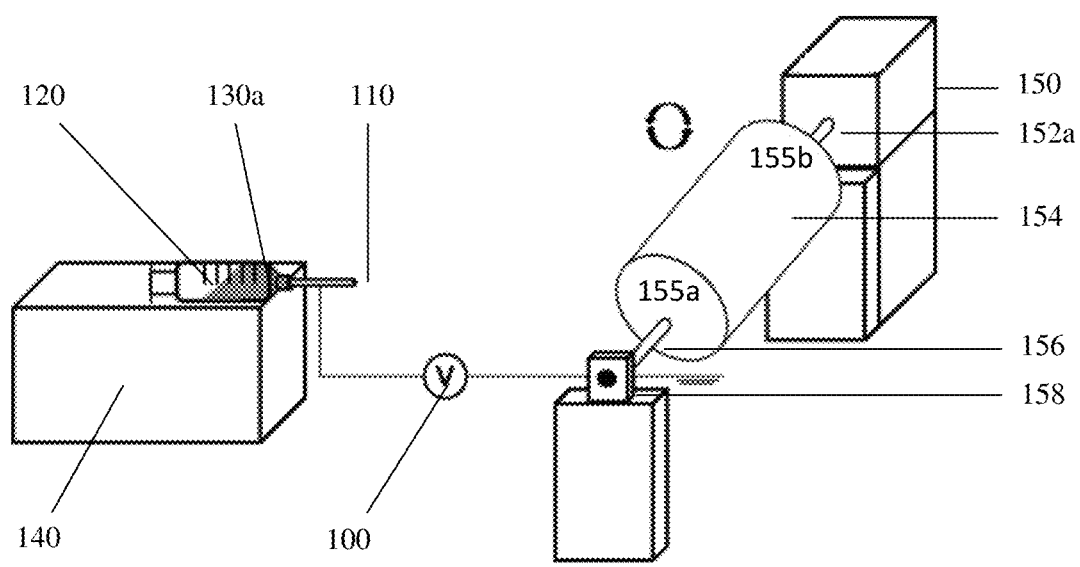
FIG. 1A is a schematic of the electrospinning system configuration to make electrospun fiber mat on a static or rotatable drum collector. A high voltage 100 is applied to a needle or injector 110 on a syringe 120 which holds a type of polymer solution 130a in the syringe barrel. The syringe is controlled by a pump 140. A motor 150 connects to a cylindrical collector (herein denoted as a drum) 154 via an adaptor 152a between the motor 150 and one end of the drum collector 155a. The other end of the cylindrical collector 155b connects to a stand-alone collector 158 via an adaptor 156.

The term "mechanical strength", as used herein, refers to any one of ultimate tensile strength (maximum stress bared until failure (N)), peak load, load at yield, tenacity, initial stiffness (N/mm), or the modulus of elasticity (Young's modulus). The modulus of elasticity measures an object or substance's resistance to being deformed elastically (i.e., non-permanently) when a force is applied to it. The elastic modulus of an object is defined as the slope of its stress-strain curve in the elastic deformation region. It can be measured using the following Formula: E=Stress/Strain, where Stress is the force causing the deformation divided by the area to which the force is applied and Strain is the ratio of the change in some length parameter caused by the deformation to the original value of the length parameter. The modulus of elasticity is presented in Pascals (Pa), or megapascals (MPa).

The term "attached", as used herein, refers to the connection of elements in a system, generally via a mechanical means including, but not limited to, a clamp, a claw, a clip, an interlock, a screw, a magnetic attraction, an adhesive, or a vacuum suction. In some embodiments, "attached" can refer to elements that are already an integral piece of a whole device. It is interchangeable with "connected" as used herein.

The term "grounded" generally refers to the status of connection to a ground. In electrical engineering, ground or earth is the reference point in an electrical circuit from which voltages are measured, a common return path for electric current, or a direct physical connection to the Earth. Therefore "grounded" as used herein in relation to electrospinning refers a collector acting as an electrode that is connected to ground or earth, as compared to a positive electrode (e.g., a charged needle tip or nozzle).

The term "collector" as used herein refers to a device where electrically charged solution, jet, melt, or gel is deposited onto in an electric field. Generally the collector is grounded, so as to provide a grounded electrode (that is apart from a positive electrode (e.g., electrically charged needle tip or nozzle)). The "collector" may also refer elements that attach or connect to the device where electrically charged solution, jet, melt, or gel is deposited onto, where the whole is electrically connected and grounded.

The term "chuck" as used herein refers to a type of clamp used to hold an object with radial symmetry (e.g., a cylinder), and herein may be mechanically and electrically connected via an adaptor to a rotator, in forming a part of a grounded collector. For examples, in drills, a chuck holds the rotating tool or workpiece.

The terms "a stand" and "a mount", as used herein, are generally interchangeable, and they refer to conductive, and generally grounded, part that a charged polymer jet can deposit onto.

The term "therapeutic agent" refers to an agent that can be administered to prevent or treat one or more symptoms of a disease or disorder.

The term "diagnostic agent", as used herein, generally refers to an agent that can be administered to reveal, pinpoint, and define the localization of a pathological process.

The term "prophylactic agent", as used herein, generally refers to an agent that can be administered to prevent disease or to prevent certain conditions like pregnancy.

The phrase "pharmaceutically acceptable" refers to compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" refers to pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient.

The term "biodegradable" as used herein, generally refers to a material that will degrade or erode under physiologic conditions to smaller units or chemical species that are capable of being metabolized, eliminated, or excreted by the subject. The degradation time is a function of composition and morphology. Degradation times can be from hours to years.

The term "biocompatible" as used herein, generally refers to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

The term "degrade", as used herein, refers to a reduction in one or more properties of the polymer over time. The one or more properties are the molecular weight, total mass, mechanical strength, elasticity, or the density or porosity of the fibers formed from polymers. The prevailing mechanism of degradation of biodegradable polymer is chemical hydrolysis of the hydrolytically unstable backbone. In a bulk eroding polymer, the polymer network is fully hydrated and chemically degraded throughout the entire polymer volume. As the polymer degrades, the molecular weight decreases. The reduction in molecular weight is followed by a decrease in mechanical properties (e.g., strength) and scaffold properties. The decrease of mechanical properties is followed by loss of mechanical integrity and then erosion or mass loss (Pistner et al., *Biomaterials*, 14: 291-298 (1993)).

As used herein, the term "active agent" or "biologically active agent" are used interchangeably herein to refer to a chemical or biological compound that induces a desired pharmacological and/or physiological effect, which may be prophylactic, therapeutic or diagnostic.

Use of the term "about" is intended to describe values either above or below the stated value in a range of approximately +/−10%. The preceding ranges are intended to be made clear by context, and no further limitation is implied.

II. Electrospinning System

In the electrospinning system, a charged polymer jet is ejected from a source of a small diameter (e.g., needle, nozzle, injector), and collected on a rotatable, grounded collector or collected in between two grounded collectors. An electrostatic charge is applied to the needle to overcome the surface tension of the solution. Usually, the concentration of the polymer solution in electrospinning is greater than a minimum concentration for any given polymer, termed the critical entanglement concentration, below which a stable jet cannot be achieved and no nanofibers will form, although nanoparticles may be achieved (electrospray) (Leach M K, et al., *J Vis Exp.*, (47): 2494 (2011)).

1. Collectors

Parallel or substantially parallel (in height), grounded collectors can be used in the electrospinning system for the charged polymer jets to deposit on.

A. Chuck

A drill chuck can rotate objects for coating by electrospun fibers, or rotate and twist formed fibers with one end held on the drill chuck.

Typically, one grounded, drill chuck is paralleled in height by an opposing, stationary, grounded collector, and the latter can be of any geometry such as a plate or a cone. This pair of collectors allows for the polymer jet to deposit in the air gap, where one end of the deposited nano- or micro-fibers is attached to the drill chuck and the other end attached to the standalone parallel collector.

In other embodiments, the drill chuck holds objects of varying diameters, e.g., 1 mm, 10 mm, 100 mm, 1 cm, 10 cm, or even greater. When objects with a hollow interior are directly held by the drill chuck, objects of even thinner diameters in the micron range (e.g., wires of diameters about 50 µm, 60 µm, 70 µm, 80 µm, 90 µm or 100 µm) can be further attached or inserted to the first object. For example, when two drill chucks are paralleled, holding both ends of a substrate (e.g., wire, thread), the electrospun fibers can coat the surface of the substrate in between drill chucks.

Drill chucks can be of varying dimensions, so long as they fit into a motor or an adaptor for a motor and rotate clockwise or counter-clockwise.

B. Cylindrical Rod

Rotating collectors, such as cylindrical rods, can be held on two ends by opposing mounts. These rotating collectors may be long cylindrical small diameter collectors (e.g., 0.8 mm, 1 mm, 2 mm, 5 mm, 10 mm in diameter) for collecting thread. They may also be mandrel collectors, grooved collectors (for making well aligned fiber sheets), or disk collectors.

In some embodiments, the cylindrical rod is used for other types of collectors (e.g., drums) or devices to clamp onto. When the cylindrical rod rotates, the collectors or devices are deposited with a layer or layers of fibers.

C. Drums

In specific embodiments, drum collectors are used for collecting sheets of fibers. The drums can be of varying sizes, e.g., about 5 cm, 10 cm, 15 cm, 20 cm, 25 cm, 30 cm, 40 cm, 50 cm, 60 cm, 70 cm, 80 cm, 90 cm, or 100 cm in diameter.

2. Adaptors

Adaptors can be used to connect a type of collectors to the motor, and facilely interchange between collector types. Specifically, they can be used to connect a type of collectors to the shaft of the motor.

Figure 1B:
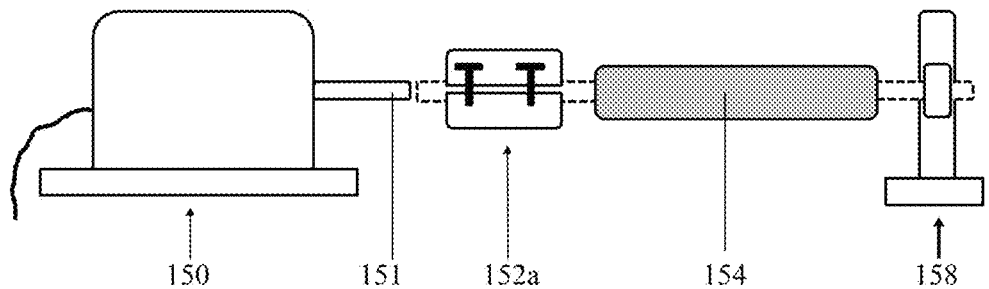
FIG. 1B is a schematic of the cross-sectional longitudinal side view of an exemplary cylindrical rod setup, including a cylindrical rod 154 (which a drum can attach to and rotate with), an adaptor 152a between the rod 154 and a motor shaft 151, and a motor 150.
Figure 12A:
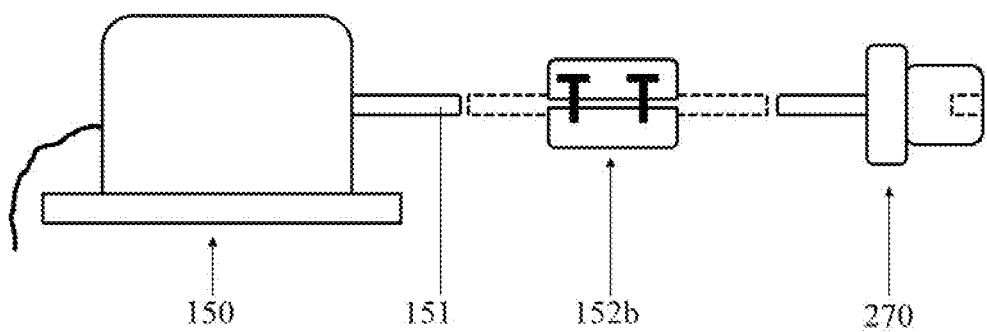
FIGS. 12A and 12B are schematics of the side-view of an exemplary drill chuck setup (FIG. 12A, longitudinal side view), including a chuck 270, an adaptor 152b between the chuck 270 and the motor shaft 151, and a motor 150; and an exemplary adaptor 152b in a cross-sectional view (FIG. 12B, cross-sectional view).
Figure 12B:
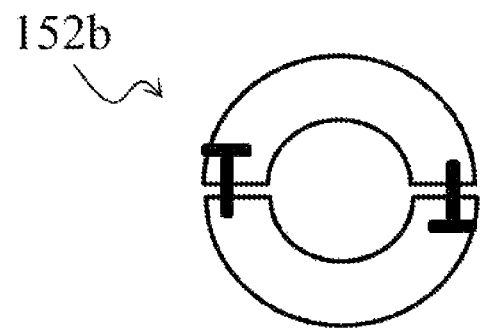

An exemplary adaptor is shown in FIGS. 12A, 12B, and 1B, which can be used to connect a cylindrical rod or a drill chuck to the motor. Adaptors can be made which are capable of connecting motor shafts from as small as 0.2 inches to several inches. The adaptor can connect the motor shaft to another device (rod) or connection to a device of the same range in size.

3. Motor

One or two motors can be connected to one or both opposing collectors. Generally, a motor has a shaft to allow for connection with specific collectors via the adaptor. Generally, the motor is capable of providing clock-wise or counterclock-wise rotation up to a speed of 1,000 revolutions per minute (rpm), 2,000 rpm, 3,000 rpm, 4,000 rpm, 5,000 rpm, 6,000 rpm, 7,000 rpm, 8,000 rpm, 9,000 rpm, 10,000 rpm, or greater.

One embodiment provides that a drum collector is clamped onto the cylindrical rod, and the cylindrical rod is connected the motor which permits the rotation of the drum collector.

Another embodiment provides that the collector pair is a drill chuck and a parallel grounded stand, and the drill chuck is connected to a motor to allow for the rotation and twisting of parallel fibers formed between the drill chuck and the stationary, parallel stand.

4. Needle, Nozzle or Injector

A polymer sol-gel, solution, suspension or melt may be loaded into the electrospinning ejection device (e.g., needle on a syringe, nozzle).

The needle can be standard needles from 34 gauge to 7 gauge (the larger the number the smaller the diameter).

In some embodiments, multiple needles are used to generate multiple streams of polymer jets towards the collectors.

The needles or syringes where the needles are attached to can be mounted onto a motorized platform, e.g., a stage, a dispenser, to allow for alterations in the configuration of the system or movement of the needles.

III. Use of Apparatus

1. Rotation, Twisting and Braiding of Fibers

A. Rotation

In some embodiments, when one or both ends of a collector, e.g., a cylindrical rod or a drum collector, are connected to a motor or motors, the cylindrical rod or drum collector can rotate about its axis. This is used for formation of a layer or layers of fiber sheets, with a curvature depending on the diameter of the rotating collector.

In an alternative embodiment, the fibers deposit on a cylindrical template, e.g., a wire, a rod, or a drum collector, to form a thickness of fibers, where the template is later removed to give rise to a hollow tubular structure that is used as a stent, tube, or vessel.

An alternative embodiment provides that a device is be clamped onto the cylindrical rod(s), fixed to the drill chuck(s), or otherwise attached to the motor(s), on one end or preferably on both ends, such that the device is rotated while electrospun fibers deposit on its surface and form a coating of polymers.

Generally a high speed of rotation leads to aligned fibers, e.g., at about 1,000 rpm, 1,100 rpm, 1,200 rpm, 1,300 rpm, 1,400 rpm, 1,500 rpm, 2,000 rpm, 3,000 rpm, or greater. A relatively low speed of rotation or stationary configuration leads to randomly positioned fibers. The threshold of rotation speed for the alignment of fibers is related to the speed of rotation, distance between jet needle/nozzle and the collect, the polymer composition and its viscosity in the electrospun solution, and other physical and chemical parameters such as the voltage and the needle/nozzle gauge.

B. Twisting

Some embodiments provide that the charged polymer jet deposits in the air gap between a drill chuck (grounded) and another parallel, grounded collector. Even when the drill chuck is attached to needles or substrates that protrude into the air gap between the drill chuck and the parallel collector, charged polymer jets can deposit in between, where fibers are formed with one end attached to the drill chuck and the other end attached to the standalone parallel collector.

An end of the fibers can be held tightly within a drill chuck. As the charged polymer jet continues to stream, hundreds of parallel fibers are formed between the chuck and the parallel collector. The individual fibers can be so thin that they are able to align the internal polymer chains without the use of heat treatment or extrusion to provide increased strength. Optionally, individual fibers can be heated to above the polymer's glass transition temperature to strengthen and harden the fibers.

With one fiber or hundreds of parallel fibers in between the drill chuck and the parallel collector, the chuck can rotate in one direction, e.g., clockwise, to twist these fibers, while the other end is held stationary on the parallel collector. In other embodiments, when the parallel collector is also connected to a motor or is a second drill chuck that is connected to a motor, rotations on both ends of the fiber(s) (e.g., in opposite directions) can also twist the fibers.

The twisted fibers can optionally be further twisted in the opposite direction, e.g., counterclockwise, to ensure that the twisted fibers do not coil or snap.

When a drill chuck is rotated 360° relative to the opposing collector, one twist is done to the fiber(s). To form densely twisted fibers of sufficient strength, hundreds, the fibers can be twisted thousands or tens of thousands of twists. For example, when the distance between the drill chuck and the opposing collector is about 50 cm, 60 cm, 70 cm, 80 cm, 90 cm, or 100 cm, twists of increasing numbers can be done to the fibers, e.g., 500 twists, 1,000 twists, 1,500 twists, 2,000 twists, 2,500 twists, 3,000 twists, 3,500 twists, and 4,000 twists, or even greater. As the number of twists increases, the diameter of the overall fiber bundle generally decreases, and the strength generally increases. The number of twists needed to meet certain strength parameters will vary depending on the composition of the polymer/drug, and the size of individual fibers. For example, with fibers made from a high molecular weight (e.g., 220 kDa) PLLA, twists ranging from 2,000 to 4,000 are generally needed to generated twisted fibers that meet the strength requirement for sutures according to United States Pharmacopeia (USP). Alternately, certain types of PCL, with or without certain drugs, can be twisted at a lower number, e.g., much below 1,575 twists, and still surpass strength requirements. One can increase the number of twists and decrease the diameter while maintaining strength. In some embodiments, including active agents up to about 5%, 10%, 15%, 20%, 25%, 30% or even greater, can still meet USP requirements for strength.

C. Braiding

A braid is an organization of three or more fibers or fiber bundles intertwined in such a way that no two fibers (or fiber bundles) are twisted around one another. Fibers can be removed from the collector(s) and placed into braiding machines known in the art to form braids of fibers. This electrospinning setup is technically twisting rather than braiding. One can collect several composite fibers and attach then to the drill chuck or to a standstill or rotating parallel stand and simply rotate the drill chuck to twist the composite fibers together in the same way that individual nanofibers were twisted together to manufacture the composite fiber.

A component of a system for removing a fiber from a collection surface needs not be in the illustrated form. Any suitable component can be included to remove the fibers such as, without limitation, a blade, a wedge, a plate, or any other shaped device that can be utilized to shear or cut the fiber from the collection surface.

2. Configuration of Apparatus

Generally, the parallel collectors are in a lined up position that is perpendicular to the needle or nozzle. The needle or nozzle can be 90°, 85°, 80°, 75°, 70°, 65°, 60°, 55°, 50°, 45°, 40°, 35°, 30°, or at another non-parallel angle with respect to the one or more grounded collectors. The distance between the end of a needle or the tip of a nozzle and the collectors can be between about 5 cm and about 100 cm, or even greater. In some embodiments, this distance is between about 5 cm and about 25 cm.

Figure 2:
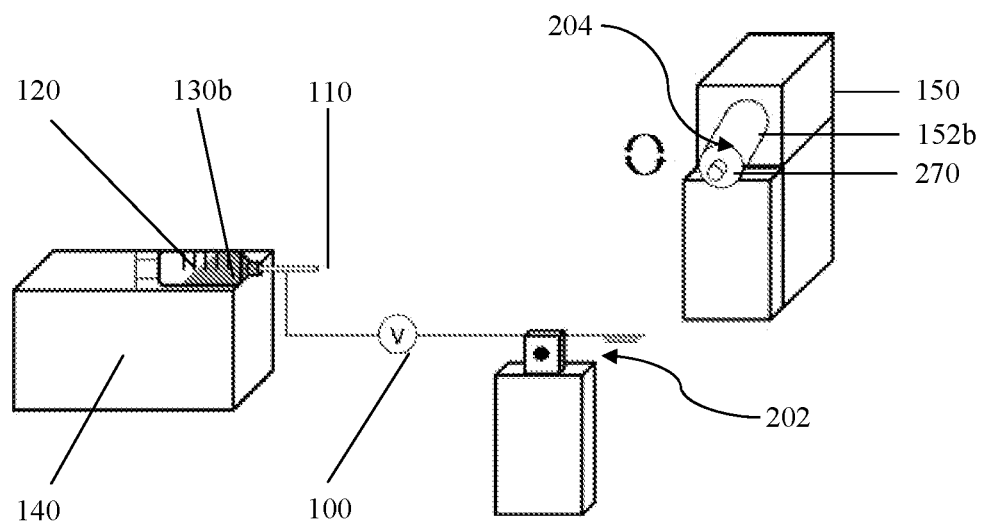
FIG. 2 is a schematic of the electrospinning configuration to make and twist electrospun fibers. Common elements to those in FIG. 1A are presented in FIG. 2. In this configuration, the motor 150 through its shaft 151 (shaft not visible in FIG. 2, but shown as element 151 in FIG. 12A) connects to a drill chuck 270 via an adaptor 152b, where the motorized grounded drill chuck as a whole serves one collector 204. A stand-alone, parallel grounded collector 202 is located in some distance from the grounded collector 204. The gap between the two grounded collectors allows polymer jet 130b extruded from the charged needle 110 to deposit and accumulate, subject to motor 150—driven twisting.
Figure 10:
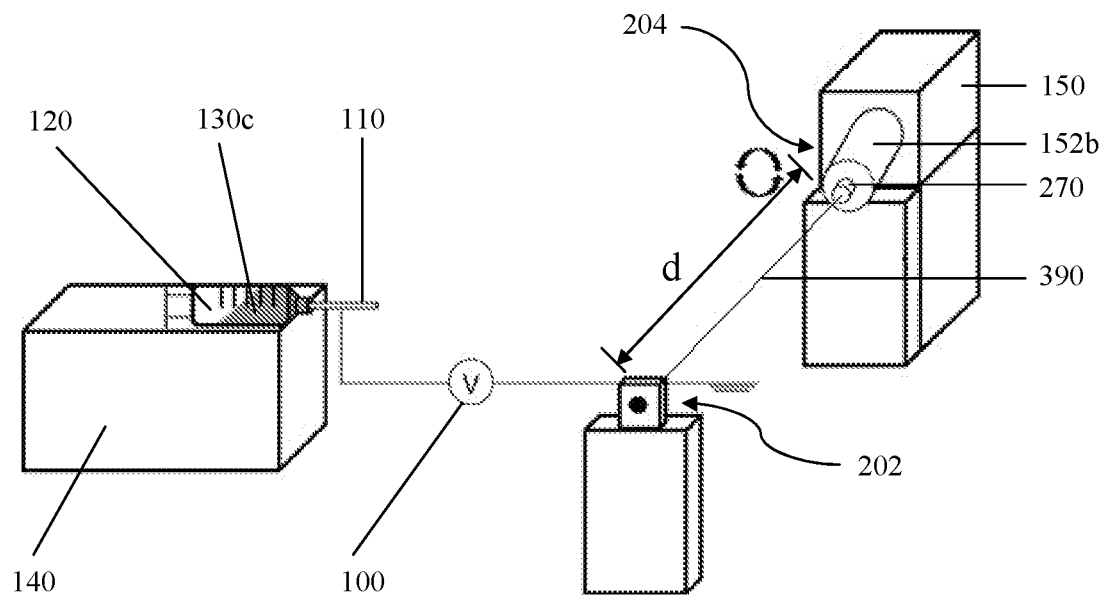
FIG. 10 is a schematic of the electrospinning configuration to coat a suture with electrospun fibers. Common elements to those in FIG. 2 are presented in FIG. 10. In this configuration, a suture has its thread 390 on one end attached to the drill chuck 270, while the needle end is held by and freely rotatable on the stand-alone, grounded collector 202. "d" refers to the distance, i.e., the length of suture thread that is between the drill chuck 270 and the stand alone, grounded collector 202.
Figure 11:
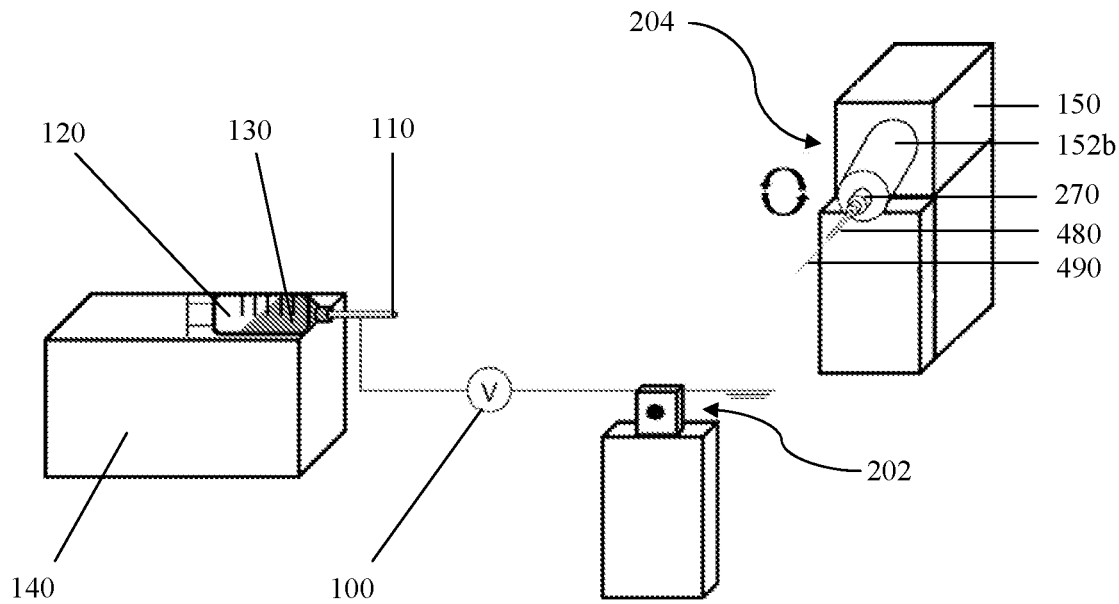
FIG. 11 is a schematic of the electrospinning configuration to make a tubular structure with electrospun fibers. Common elements to those in FIG. 2 are presented in FIG. 11. In this configuration, a syringe needle 480 is secured to the chuck 270, and a template wire 490 is securely inserted in the syringe needle 480. Extruded polymer jets may be deposited around the template wire (which is rotatable due to connection via a chuck 270 to the motor 150). A tubular structured device with a lumen diameter about the same as the template wire 490 is created by removal of the wire.

The distance between the motor and the parallel stand (d) can be between about 2 mm up to about 200 cm, or even greater, e.g. distances between a motor 150 and a parallel collector 158 in FIG. 1A, between a motor-connected collector 204 and a stand-alone parallel collector 202 in FIGS. 10, 2, and 11. Maximum possible distance is generally understood to be related to fiber diameter, as well as other formation parameters. In some embodiments, the distance between the collectors is from about 50 cm to about 100 cm.

Generally, the heights of the collectors are about the same, i.e., parallel collectors. In other instances, the heights of the opposing collectors can be of different heights, by difference of 10%, 20%, 30%, 40% or greater, of the taller collector.

The height of the needle or nozzle where the polymer jet starts can be the same or different from the heights of the collectors. Electrically charged polymer jets may be extruded or sprayed from a single nozzle or multiple nozzles towards grounded collectors. In preferred embodiments, the height of the needle is greater than that of the parallel collectors. In one embodiment, the needle is pointed in a horizontal orientation, and in another embodiment, the needle is pointed in a vertical orientation. The angle that the needle pointed at with respective to the horizontal level can be 0°, 10°, 20°, 30°, 40°, 50°, 60°, 70°, 80°, or 90°, preferably from a height no shorter than the height of the collectors.

A polymer solution (optionally containing a therapeutic, prophylactic or diagnostic agent) 130 can be held in a syringe 120 that is controlled by a programmable syringe pump 140 known in the art. The gauge of the needle 110, the speed that the polymer solution is pushed out from the needle, and the volume of polymer to be electrospun can be tuned, according to the composition and the viscosity of the solution, the configuration of the collectors, and the desired properties of formed fibers. In some embodiments, multiple needles are used to generate multiple streams of polymer jets on the collectors.

The syringe pump can also be mounted onto a plexiglass base atop a motorized stage known in the art. This controls the motion of the needle in the x direction and the y direction. Moving along an x-direction may position the needle closer or farther away from the collectors, while moving along an y-direction may position the needle at a constant distance from the center-line of the parallel collectors.

The critical field strength required to overcome the forces due to surface tension of the solution and form a jet will depend on many variables of the system. These variables include not only the type of polymer and solvent, but also the solution concentration and viscosity, as well as the temperature of the system. In general, characterization of the jet formed, and hence characterization of the fibers formed, depends primarily upon solution viscosity, net charge density carried by the electrospinning jet and surface tension of the solution. The ability to form the small diameter fibers depends upon the combination of all of the various parameters involved. For example, electrospinning of lower viscosity solutions will tend to form beaded fibers, rather than smooth fibers. In fact, many low viscosity solutions of low molecular weight polymers will break up into droplets or beads, rather than form fibers, when attempts are made to electrostatically spin the solution. Solutions having higher values of surface tension also tend to form beaded fibers or merely beads of polymer material, rather than smooth fibers. Thus, the preferred solvent for any particular embodiment will generally depend upon the other materials as well as the formation parameters, as is known in the art.

In some embodiments, the system is placed inside a sterile containment system such as a traditional cell culture hood, allowing for sterile production of electrospun fibers.

Additional elements can be included with the electrospinning system. For example, a strip heater, fan, or a temperature controller can be added to allow for temperature control.

Different configurations, e.g., single needle single jet, single needle multi-jets, multi-needle multi-jets, or even needleless configurations for electrospinning may be used to fabricate polymeric nanofibers, which later are twisted by rotating two ends of the bundle of nanofibers in different angular speed and/or in different angular directions. Other techniques may also be used to fabricate aligned or twisted polymeric nanofibers, such as meltblowing, bicomponent spinning, forcespinning, and flash-spinning, when at least one collector can be rotated.

Meltblowing

In a meltblowing process, a molten polymer is extruded through the orifice of a die. The fibers are formed by the elongation of the polymer streams coming out of the orifice by air-drag and are collected on the surface of a suitable collector in the form of a web. The average fiber diameter mainly depends on the throughput rate, melt viscosity, melt temperature, air temperature and air velocity. Nanofibers can be fabricated by special die designs with a small orifice, reducing the viscosity of the polymeric melt and suitable modification of the meltblowing setup. To reduce or prevent the sudden cooling of the fiber as it leaves the die before the formation of nanofibers, hot air flow may be provided in the same direction of the polymer around the die. The hot air stream flowing along the filaments helps in attenuating them to smaller diameter. The viscosity of polymeric melt can be lowered by increasing the temperature.

Template Melt-Extrusion

In template melt-extrusion, molten polymer is forced through the pores of a template (e.g., an anodic aluminum oxide membrane (AAOM)) and then subsequently cooled down to room temperature. A special stainless steel appliance may be designed to support the template, to bear the pressure and to restrict the molten polymer movement along the direction of the pores. The appliance containing the polymer was placed on the hot plate of a compressor (with temperature controlled functions) followed by the forcing of the polymeric melt. Isolated nanofibers may be obtained by the removal of the template (e.g., dissolution with appropriate solvent(s)).

Flash-Spinning

In the flash-spinning process, a solution of fiber forming polymer in a liquid spin agent is spun into a zone of lower temperature and substantially lower pressure to generate plexi-filamentary film-fibril strands. A spin agent is required for flash-spinning which 1) should be a non-solvent to the polymer below its normal boiling point, 2) can form a solution with the polymer at high pressure, 3) can form a desired two-phase dispersion with the polymer when the solution pressure is reduced slightly, and 4) should vaporize when the flash is released into a substantially low pressure zone. Flash-spinning is more suitable for difficult to dissolve polymers such as polyolefins and high molecular weight polymers. The spinning temperature should be higher than the melting point of polymer and the boiling point of solvent in order to effect solvent evaporation prior to the collection of the polymer.

Bicomponent Spinning

Bicomponent spinning is a two-step process that involves spinning two polymers through the spinning die (which forms the bicomponent fiber with island-in-sea (IIS), side-by-side, sheath-core, citrus or segmented-pie structure) and the removal of one polymer.

IV. Materials of Electrospun Fibers

Polymer solutions, sol-gel, suspension or melt may be loaded into the electrospinning ejection device (e.g., needled syringe, nozzle). Solutions and melts can include homopolymers, block copolymers, random copolymers, or polymeric blends.

Mixtures of materials can be electrospun to form composite fibers. For example, a solution including one or more polymers in combination with a non-polymeric additive can be electrospun to form composite fibers. Additives are generally selected based upon the desired application of the formed fiber structures. For example, one or more polymers can be electrospun with a therapeutic, prophylactic and/or diagnostic agent that can be polymeric or non-polymeric. Additives can be incorporated in the fibers during formation as is known in the art, for example, as described in U.S. Pat. No. 6,821,479 to Smith, et al., U.S. Pat. No. 6,753,454 to Smith, et al., and U.S. Pat. No. 6,743,273 to Chung, et al.

A. Polymers

In some embodiments, polymers that have been found suitable for use in biological or medical applications can be utilized. These may be degradable under physiological conditions. Non-degradable polymers can be utilized alone, in combination, or in sequence with degradable polymers.

A polymeric solution that is loaded into an electrospinning nozzle or syringe can include any suitable solvent. Selection of solvent can be important in determining the characteristics of the solution, and hence of the characteristic properties of the nanofibers formed during the process. Examples include hexafluoroisopropanol, methanol, chloroform, dichloromethane, dimethylformamide, acetone, acetic acid, acetonitrile, m-cresole, tetrahydrofuran (THF), toluene, as well as mixtures of solvents.

Preferred polymers including polyhydroxy acids such as poly(lactic acid), poly(glycolic acid) and poly(lactic-co-glycolic acid), polycaprolactone, polydioxanone, as well as combinations of polymers (i.e., poly-1-lactic acid/polyethylene glycol) having a molecular weight between 1 kDa and 500 kDa.

Other examples of suitable biodegradable, biocompatible polymers include polyhydroxyalkanoates such as poly-3-hydroxybutyrate or poly-4-hydroxybutyrate; poly(orthoesters); polyanhydrides; poly(phosphazenes); poly(lactide-co-caprolactones); polycarbonates such as tyrosine polycarbonates; polyamides (including synthetic and natural polyamides); polyesteramides; other polyesters; poly(dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyalkylene) polymers such as polyethylene glycol and block polymers thereof such as poly(oxypropylene) copolymers; polyketals; polyphosphates; polyhydroxyvalerates; polyalkylene oxalates; polyalkylene succinates; poly(maleic acids), as well as copolymers thereof.

The biodegradable, biocompatible polymer can be a polylactic acid polymer or copolymer containing lactide units substituted with alkyl moieties. Examples include, but are not limited to, poly(hexyl-substituted lactide) or poly(dihexyl-substituted lactide).

In the most preferred embodiments, the biodegradable polymer is polyglycolide or poly-(D,L-lactide-co-glycolide) such as poly-(D,L-lactide-co-glycolide) containing about 55 to about 80 mole % lactide monomer and about 45 to about 20 mole % glycolide and poly-(D,L-lactide-co-glycolide) containing about 65 to about 75 mole % lactide monomer and about 35 to about 25 mole % glycolide. The poly-(D,L-lactide-co-glycolide) can contain terminal acid groups.

The molecular weight of the polymer can be varied to optimize the desired properties, such as drug release rate, for specific applications. The one or more biodegradable, biocompatible polymers can have a molecular weight of about 1 kDa to 500 kDa. In certain embodiments, the biodegradable, biocompatible polymers has a molecular weight of between about 10 kDa and about 300 kDa, more preferably between about 50 kDa and about 200 kDa.

Non-degradable polymers include ethylene vinyl alcohol copolymers (EVOH), polyurethanes, silicones or silicon elastomers, polyesters, polyolefins, polyisobutylene and ethylene-alpha olefin copolymer, a styrene-isobutylene-styrene triblock copolymers, acrylic polymers and copolymers, vinyl halide polymers and copolymers, polyvinyl chloride, polyvinyl ethers, polyvinyl methyl ether, polyvinylidene halides, polyvinylidene fluoride, polyvinylidene chloride, polyfluoro alkene, poly perfluorinated alkene, polyacrylonitrile, polyvinyl ketones, polyvinyl aromatics, polystyrene, polyvinyl esters, polyvinyl acetates, copolymers of vinyl monomers each other and olefins, ethylene-methyl methacrylate copolymers, acrylonitrile-styrene copolymers, ABC resins and ethylene-vinyl acetate copolymers, polyamides such as nylon 66 and polycaprolactam, alkyd resins, polyoxymethylenes; polyimides; polyethers, epoxy resins, rayon, rayon-triacetate and a biocompatible polymer according to claim 1 selected from the group consisting of a combination thereof.

B. Therapeutic, Prophylactic or Diagnostic Agents

The fibers may include one or more therapeutic, prophylactic, or diagnostic agents that are encapsulated, conjugated to the polymer in a solution before electrospinning, or encapsulated in/conjugated to sustained release nanoparticle/microparticle formulations that are entrapped in between or conjugated with the formed fibers. These may be proteins, peptides, nucleic acid, carbohydrate, lipid, or combinations thereof, or small molecules. Suitable small molecule active agents include organic and organometallic compounds. In some instances, the small molecule active agent has a molecular weight of less than about 2000 g/mol, preferably less than about 1500 g/mol, more preferably less than about 1200 g/mol, most preferably less than about 1000 g/mol. In other embodiments, the small molecule active agent has a molecular weight less than about 500 g/mol. The small molecule active agent can be a hydrophilic, hydrophobic, or amphiphilic compound. Biomolecules typically have a molecular weight of greater than about 2000 g/mol and may be composed of repeat units such as amino acids (peptide, proteins, enzymes, etc.) or nitrogenous base units (nucleic acids). In preferred embodiments, the active agent is an ophthalmic therapeutic, prophylactic or diagnostic agent.

Representative therapeutic agents include, but are not limited to, anti-fibrotic/anti-scarring, anti-inflammatory drugs, including immunosuppressant agents and anti-allergenic agents, anti-infectious, and anesthetic agents. Some examples of anti-inflammatory drugs include triamcinolone acetonide, fluocinolone acetonide, prednisolone, dexamethasone, loteprendol, fluorometholone. Immune modulating drugs such as: cyclosporine, tacrolimus and rapamycin. Non steroidal anti inflammatory drugs include ketorolac, nepafenac, and diclofenac. Antiinfectious agents include antiviral agents, antibacterial agents, antiparasitic agents, and anti-fungal agents. Exemplary antibiotics include moxifloxacin, ciprofloxacin, erythromycin, levofloxacin, cefazolin, vancomycin, tigecycline, gentamycin, tobramycin, ceftazidime, ofloxacin, gatifloxacin; antifungals: amphotericin, voriconazole, natamycin.

In some embodiments, levofloxacin, moxifloxacin, bacitracin, sirolimus, sunitinib, triamcinolone acetonide, cyclosporine, and dexamethasone are included individually or in combination in the formulations.

For ophthalmology applications, active agents can include anti-glaucoma agents that lower intraocular pressure (IOP), anti-angiogenesis agents, growth factors, steroidal drugs, and combinations thereof for treatment of vascular disorders or diseases. Examples of anti-glaucoma agents include mitomycin C, prostaglandin analogs such as travoprost and latanoprost, prostamides such as bimatoprost; beta-adrenergic receptor antagonists such as timolol, betaxolol, levobetaxolol, and carteolol, alpha-2 adrenergic receptor agonists such as brimonidine and apraclonidine, carbonic anhydrase inhibitors such as brinzolamide, acetazolamine, and dorzolamide, miotics (i.e., parasympathomimetics) such as pilocarpine and ecothiopate), seretonergics, muscarinics, and dopaminergic agonists.

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

In some cases, the agent is a diagnostic agent for imaging or otherwise assessing the tissue of interest. Examples of diagnostic agents include paramagnetic molecules, fluorescent compounds, magnetic molecules, and radionuclides, x-ray imaging agents, and contrast media.

The agents may be present in their neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

The agent or agents can be directly dispersed or incorporated into the fibers as particles using common solvent with the polymer, for example, microparticles and/or nanoparticles of drug alone, or microparticles and/or nanoparticles containing a matrix, such as a polymer matrix, in which the agent or agents are encapsulated or otherwise associated with the particles.

The concentration of the drug in the finished fibers or formed structures of fibers can vary. In some embodiments, the amount of drug is between about 0.1% and about 75% by weight, preferably between about 1% and about 20% by weight, more preferably between about 3% and about 20% by weight, most preferably between about 5% and about 20% by weight of the finished structures.

In particular embodiments, the agent is released at an effective amount to inhibit, prevent, or treat disorders or diseases in ophthalmology, cardiology, neurology among others for at least 2 weeks, 4 weeks, 6 weeks, 8 weeks, 10 weeks, 12 weeks, 16 weeks, or 20 weeks.

C. Formulations

The amount of polymer or polymers in the finished fibers can vary. In some embodiments, the concentration of the polymer or polymers is from about 75 wt % to about 85% by weight of the finished fibers. In some embodiments, the concentration of the polymer or polymers is from about 85 wt % to about 100% by weight of the finished fibers.

Representative excipients include pH modifying agents, preservatives, antioxidants, suspending agents, wetting agents, viscosity modifiers, tonicity agents, stabilizing agents, and combinations thereof. There may be residual levels of solvent. Suitable pharmaceutically acceptable excipients are preferably selected from materials which are generally recognized as safe (GRAS), and may be administered to an individual without causing undesirable biological side effects or unwanted interactions.

IV. Formed Fibers and Uses Thereof

The fibers can be formed into a variety of shapes, including fibers and filaments, multifilament fibers, twisted fibers, braided filaments, multifilaments, twisted fibers and braided bundles, or devices, such as tubes, stents, vascular grafts, and meshes, for use as prosthetics or tissue scaffolds, as well as membrane or other devices for industrial applications such as water purification. The fibers may also be used to coat any medical device of choice. Generally the device to be coated is connected to be part of the grounded collector, such that polymeric fibers are deposited onto the surface of the device. The fiber coating may provide drug-loading features, and/or surface smoothness/roughness or chemical features. Exemplary devices to be coated include a stent, a catheter, a blade, a suture, and a thread.

In one embodiment, the fibers, sheets, tubes, or sutures can be further processed following initial formation to form a structure of a specific size, shape, and/or mesh size. For example, multiple sheets can be combined together to form a larger composite sheet of a desired shape. In another embodiment, a plurality of twisted nanofibers can be braided to form a biaxial, triaxial, or unidirectional fiber bundle, in order to acquire different strengths.

The fibers can be utilized in a wide variety of applications. For example, they can be utilized in textile, biological, and electrochemical applications, among others. As-formed fibers can be combined with other materials to form composite 3-D structures. In one embodiment, the electrospun fibers can be loaded with biologically active materials, including live cells, growth factors, nutrients, and therapeutic or prophylactic agents, and can function as a 3-D tissue engineering scaffold. In another embodiment, the fibers can be woven or braided into a mat with controlled mesh size, and used as wound dressing to promote the healing process. The mesh size of the mat can be controlled by tuning the angle and density of the fibers, in order to allow penetration of nutrients and certain cell types while excluding other cell types. For example, a mat or braided bundle can have mesh pores between 0 (i.e., no porosity, for example, following compression, so that it is impermeable to fluids and gases; or slightly permeable to just gases, or permeable to fluids and gases) and about 650 mm$^2$. Average mesh pore size can be greater than about 0.5 µm$^2$, for example, between about 0.5 µm$^2$ and about 600 mm$^2$. For relatively tight braiding, the pore size is between about 1.5 µm$^2$ and about 125 µm$^2$, whereas for relatively loose braiding the pore size is between about 0.5 mm$^2$ and about 125 mm$^2$, or between about 15 mm$^2$ and about 50 mm$^2$. Individual pore sizes can be smaller, and average pore diameter can be on the micrometer scale, for example, greater than about 10 µm, in one embodiment, or between about 10 µm and about 200 µm, between about 50 µm and about 100 µm, in another embodiment.

As another example, the formed paralleled fibers are twisted, such that the overall diameter of the multifilament "bundle" decreases, e.g., 500 µm, 400 µm, 300 µm, 200 µm, 150 µm, 100 µm, 50 µm, 40 µm, 30 µm, 20 µm, or 10 µm, while increasing the tensile strength.

The present invention will be further understood by reference to the following non-limiting examples.

Example 1: Drum Collector and the Formation of Randomly Aligned Fibers into a Mat Materials and Methods As shown in FIG. 1A, a 120 W regulated high voltage DC power source 100 was applied to a 20 G blunt tip needle 110 on the end of a syringe 120. This allowed for ejection from the syringe of electrified polymer solution 130a (10 wt % solution of 80 kDa polycaprolactone dissolved in HFIP) held in the syringe 120. The flow rate of 450 µL/hr of this solution was controlled by a NE-1000 Programmable Single Syringe Pump 140 mounted onto a plexiglass base atop a motorized stage capable of controlled x- and y-direction motion. The collector was connected to a mounted 120V, ⅓ hp, 300-3, 450 rpm speed-control motor 150 (capable of clockwise or counter-clockwise rotation). An adaptor 152 was used to allow for connection of a drum collector 154 to the motor 150. The drum collector 154 was located perpendicular to the syringe. A grounded, stand-alone parallel mount 158 was connected to the other end of the drum collector via an adaptor 156. When the drum collector was in a static configuration, randomly aligned nano- or micro-fibers were deposited onto the surface of the drum collector. As shown in FIG. 1B, a cylindrical rod collector 154 may be connected to the motor 150 via an adaptor 152.

Results

The randomly aligned nano- and micro-fibers formed a "mat" with meshes, as confirmed by scanning electron microscopy (SEM). The diameter of the formed fibers was in the range of between 100 nm and 5 µm.

Example 2: Rotation of Drill Chuck, Formation of Twisted, Multi-Filament Fibers and Characterizations Materials and Methods Polycaprolactone (PCL), polylactic acid (PLLA), and poly(lactic-co-glycolic acid) (PLGA) having a molecular weight of 80 kDa; polyglycolide (PGA) and polydioxanone (PDO) used were the only commercially available polymers from Purac: Corbion and Sigma Aldrich, respectively.

PCL of different molecular weights, such as 65-75 kDa, 80 kDa, 150 kDa, and 500 kDa, were also used.

As shown in FIG. 2, a 120 W regulated high voltage DC power source 100 was applied to a 20 G blunt tip needle 110 on the end of a syringe 120. This allowed for the ejection, from the syringe, of electrified polycaprolactone solution 130b held in the syringe 120. The flow rate of 450 µL/h of this solution was controlled by a NE-1000 Programmable Single Syringe Pump 140 mounted onto a plexiglass base atop a motorized stage capable of controlled x- and y-direction motion. The drill chuck was connected to a mounted 120V, ⅓ hp, 300-3,450 rpm speed-control motor 150 (capable of clockwise or counter-clockwise rotation). The drill chuck 270 was connected to the adaptor 152b which was further connected to the motor 150. A grounded, drill chuck connected to a motor was used as a collector 204, and a standalone, parallel, grounded metal stand was used as another collector 202 in this configuration. As shown in FIG. 12A, the drill chuck was connected to the motor via an adaptor.

An exemplary drill chuck collector may be used for long continuous fibers, where one side of the collector is removable to allow for facile collection of fibers.

When a charged polymer jet was ejected from the needle, it deposited in the air gap between both collectors 204, 202. As the polymer solution continued to be ejected, hundreds of parallel fibers were formed with one end attached to the drill chuck 270 and the other end attached to the standalone parallel stand 202.

Next, the drill chuck was rotated clockwise to twist the parallel fibers into a bundle of twisted filaments.

Results

The formed bundle were examined under SEM, and overall diameter of the bundle was about 28 µm or larger. It contained hundreds of nano-fibers that were twisted in one direction and tightly packed. This thick multifilament bundle could be used as suture materials, because it was much thinner compared to regular 10-0 nylon suture and its strength was enhanced after twisting.

Figure 3:
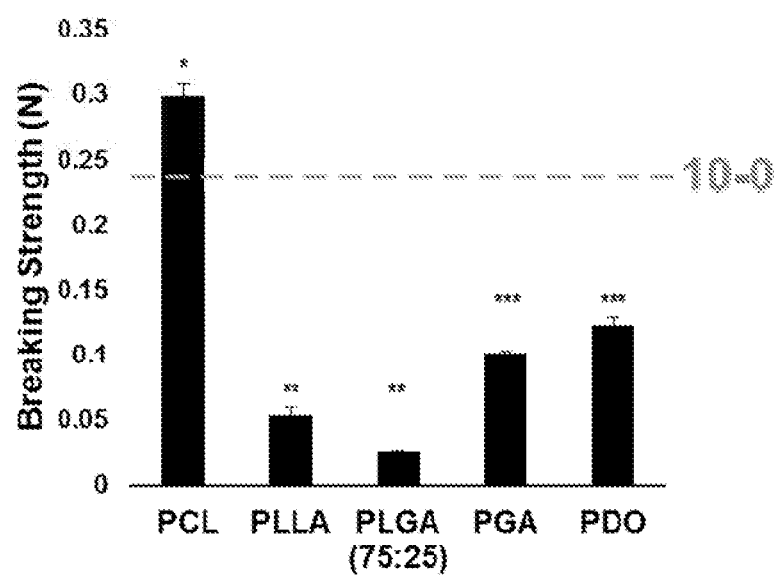
FIG. 3 is a bar graph showing the breaking strength (N) of twisted multifilaments (all with 1,575 twists, and 28 μm in diameter) formed with electrospun fibers of different polymers. (* $p<0.05$; conditions with different numbers of asterisks are statistically different with $p<0.05$. Conditions with an equivalent number of asterisks are not statistically different.) The dash line indicates the standards for sutures of USP size 10-0.

As shown in FIG. 3, for all multifilament bundles with 1,575 twists and 28 µm in diameter, the one made from PCL provided the greatest strength.

Figure 4:
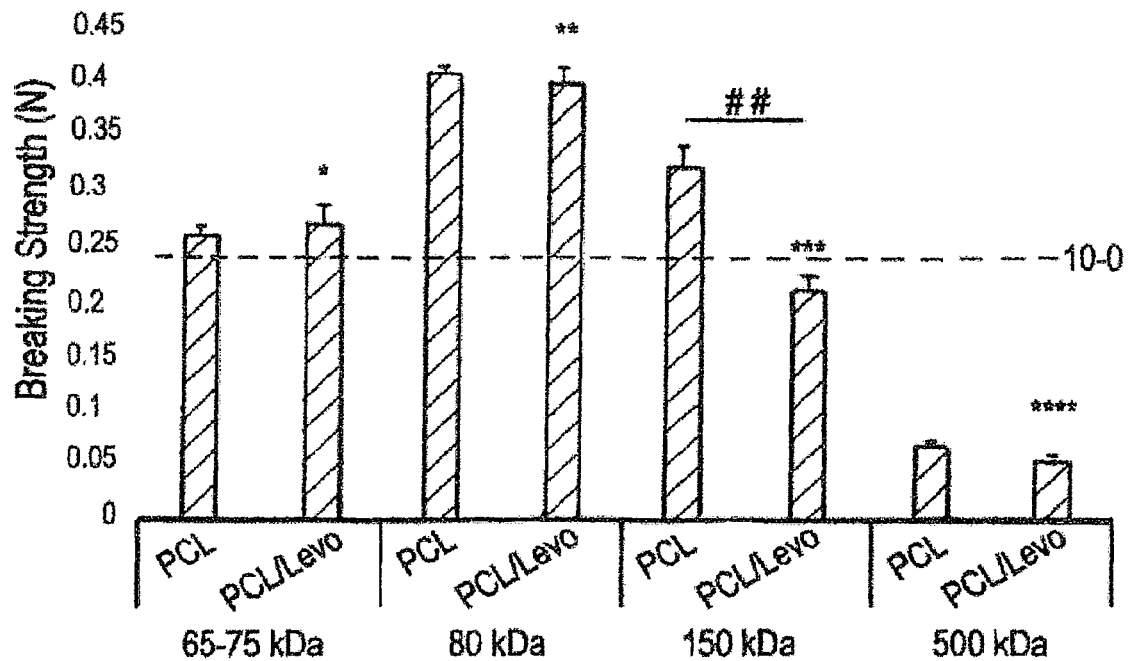
FIG. 4 is a bar graph showing the breaking strength (N) of twisted multifilaments formed with polycaprolactone (PCL) of different molecular weights, or with PCL and 8 (w/w) % levofloxacin (PCL/Levo). (Conditions with different numbers of asterisks are statistically different with $p<0.05$. ## indicates statistical significance at $p<0.01$.)

As shown in FIG. 4, multifilament bundles formed with PCL of 80 kDa provided greatest strength, and was not significantly affected by loading of levofloxacin.

Figure 5:
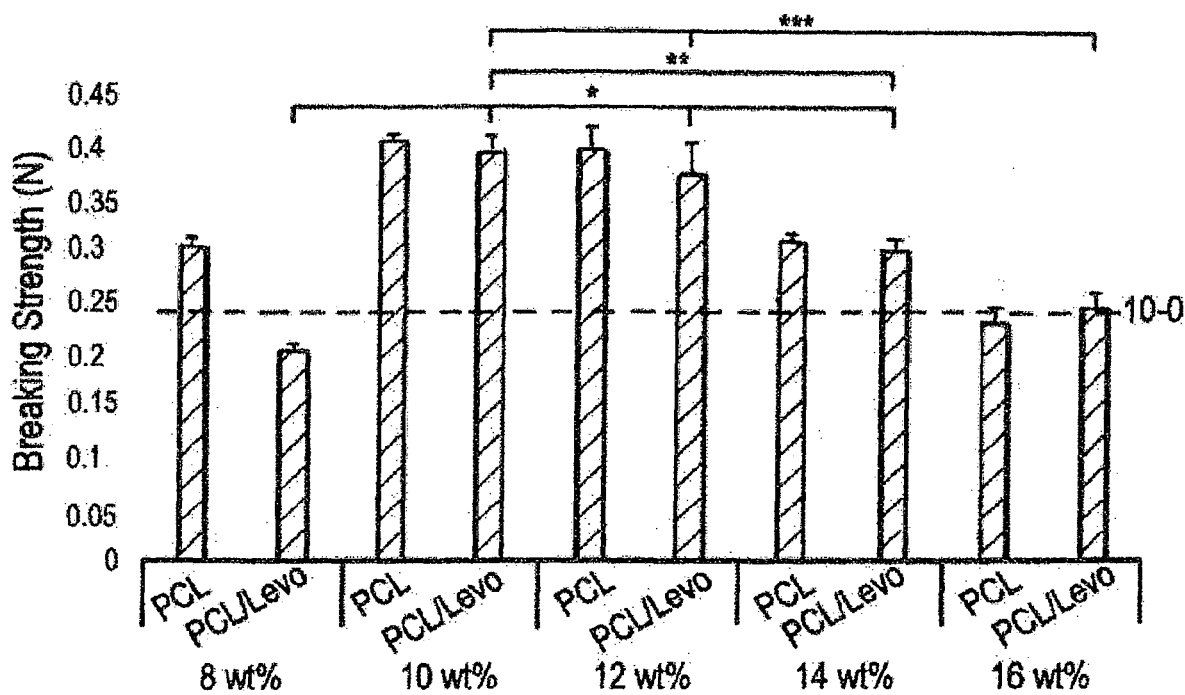
FIG. 5 is a bar graph showing the breaking strength (N) of twisted multifilaments formed with polycaprolactone (PCL) containing zero or different weight percent amounts of levofloxacin (PCL/Levo).

As shown in FIG. 5, multifilament bundles formed with PCL and/or levofloxacin, all having 1,575 twists and 28 µm in diameter had various strengths: 8 wt % PCL/Levo was significantly weaker than 10, 12, or 14 wt % PCL/Levo. 10 wt % PCL/Levo was significantly stronger than 14 wt % PCL/Levo, and 16 wt % PCL Levo was significantly weaker than 10 or 12 wt % PCL/Levo. Overall, 10 wt % and 12 wt % PCL demonstrated the highest breaking strength and were not significantly affected by loading of levofloxacin.

Figure 6:
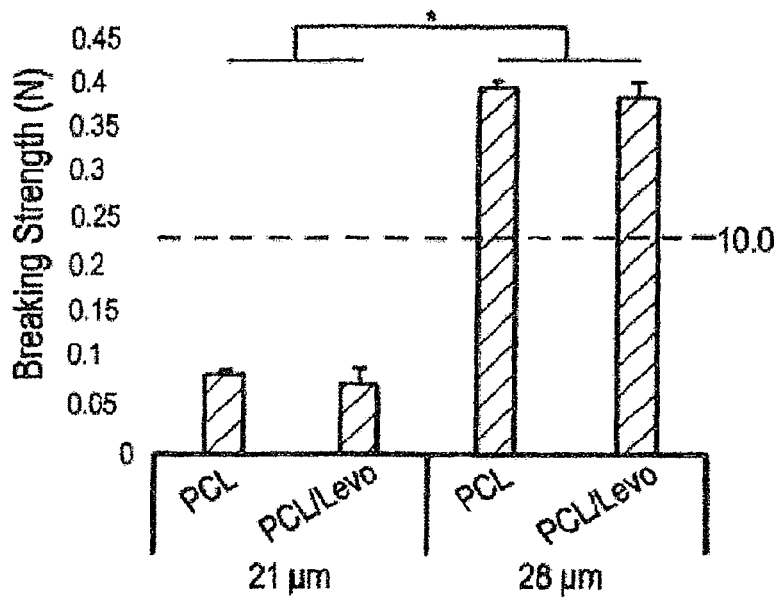
FIG. 6 is a bar graph showing the breaking strength (N) of twisted multifilaments having different diameters. The fibers were formed with PCL and optionally containing 8 (w/w) % levofloxacin.

As shown in FIG. 6, 28 µm multifilaments were significantly stronger than 21 µm multifilaments. Note both 21 and 28 µm diameters would be classified as 10-0 size for sutures.

Figure 7:
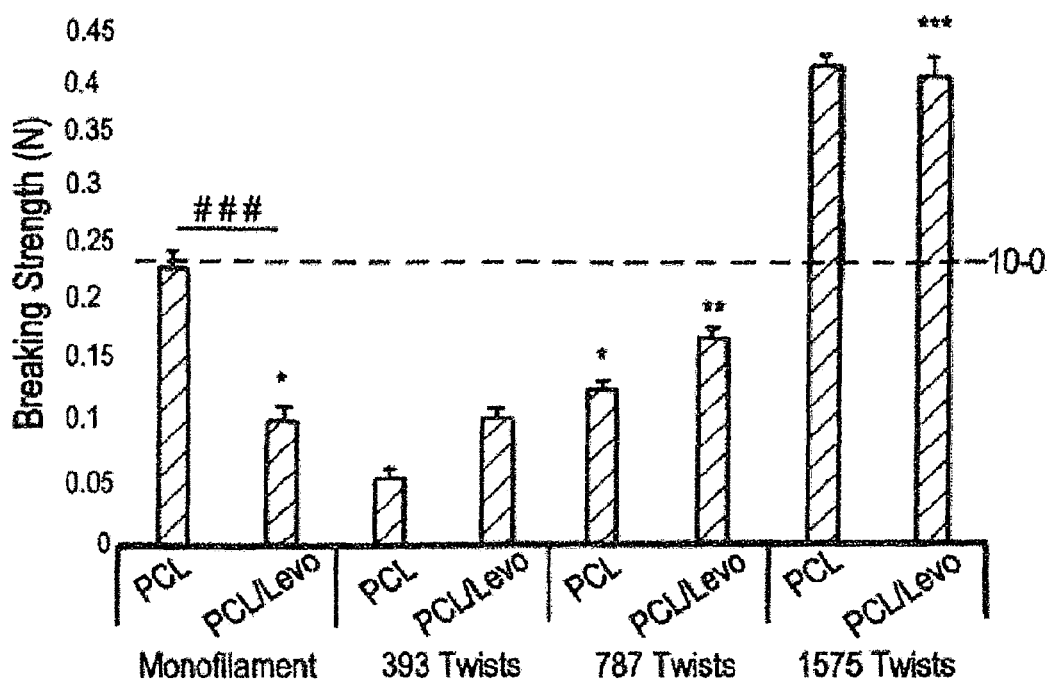
FIG. 7 is bar graph showing the breaking strength (N) of PCL multifilaments of various twists, and the filaments optionally contain 8 (w/w) % levofloxacin. (Conditions with different numbers of asterisks are statistically different to each other with $p<0.05$. Conditions with an equivalent number of asterisks are not statistically different.)

As shown in FIG. 7, there was an about 50% strength loss with the addition of drug to a monofilament; however, there was no statistically significant loss in strength with the addition of drug to the twisted, multifilament sutures. The strength of multifilaments of 1,575 twists exceeded that of the monofilament.

Figure 8:
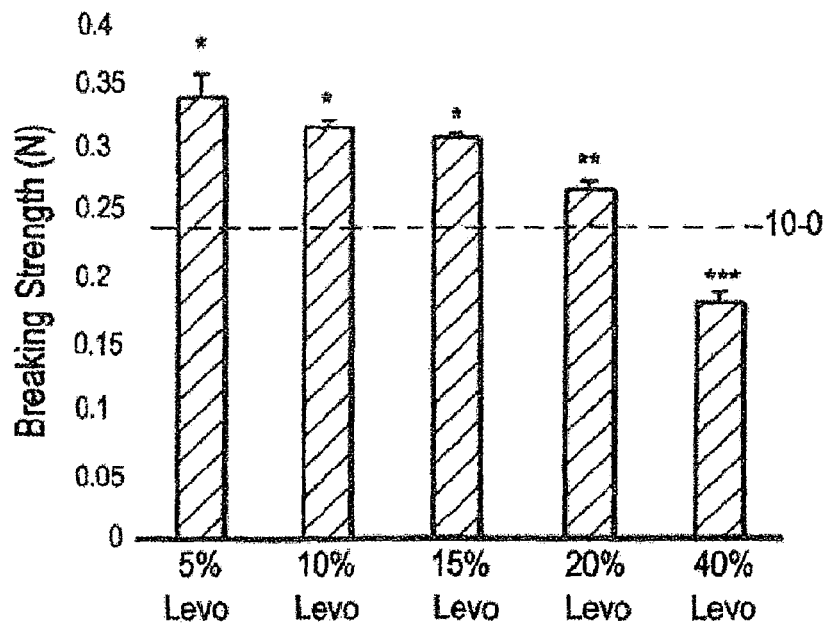
FIG. 8 is bar graph showing the breaking strength (N) of multifilaments, all 28 μm in diameter, containing different amount of levofloxacin.
Figure 9:
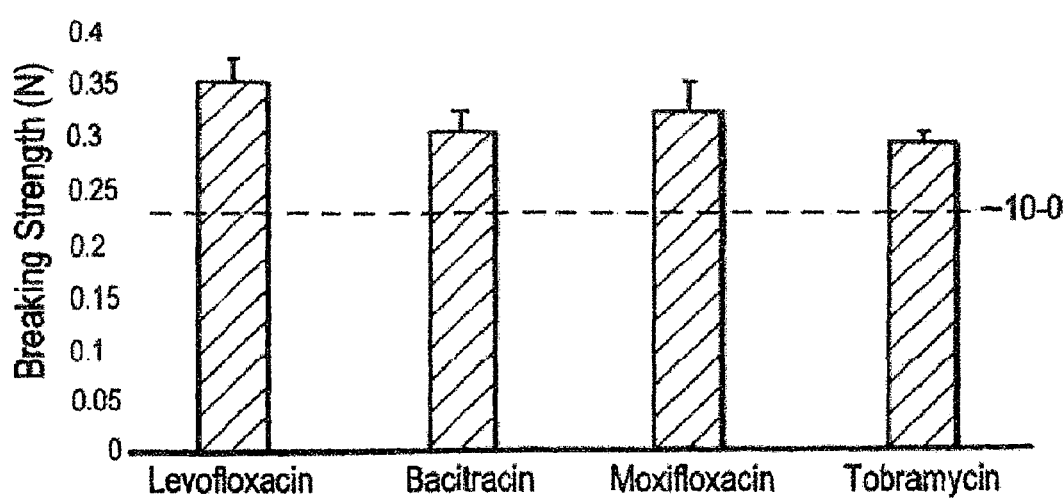
FIG. 9 is bar graph showing the breaking strength (N) of multifilaments, all 28 μm in diameter and having 1,575 twists, containing different drugs at 8 (w/w) %.

As shown in FIG. 8, loading the drug up to 20 (w/w) % maintained the strength, as required by the USP standards for 10-0 sutures. As shown in FIG. 9, multifilaments with different drugs (of different hydrophobicity) as tested at a loading of 8 (w/w) % had similar strengths, all satisfying the requirements by the USP standards for 10-0 sutures.

Example 3: Rotation of Drill Chuck to Coat a Device (Suture) with Nanofibers

Materials and Methods

As shown in FIG. 10, a 120 W regulated high voltage DC power source 120 was applied to a 20 G blunt tip needle 110 on the end of a syringe 120. This allowed for the ejection of electrified polycaprolactone solution containing sirolimus (also known as rapamycin) 130c (20% sirolimus:polycaprolactone (w/w)) was held in the syringe 120. The flow rate of 1 mL/hr of this solution was controlled by a NE-1000 Programmable Single Syringe Pump 140 mounted onto a plexiglass base atop a motorized stage capable of controlled x- and y-direction motion. A drill chuck 270 was mounted to a 120V, ⅓ hp, 300-3,450 rpm speed-control motor 150 (capable of clockwise or counter-clockwise rotation) via an adaptor 260. The grounded, drill chuck connected to the motor was used as a collector 204, and a standalone, parallel, grounded metal stand was used as another collector 202 in this example; the distance (d, of FIG. 10) between them was 17.5 cm.

The thread end of a 10-0 nylon suture 390 was fixed to the drill chuck 270. The needle end of the suture was placed through the parallel stand 202, such that this end of the suture was kept free to rotate.

After the charged polymer/drug solution was released, hundreds of the charged polymer/drug jet deposited between the chuck 270 and the parallel stand 202, surrounding the suture. Due to the electric charge, the fibers are held tightly by the chuck and the parallel stand. Then, the chuck was rotated clockwise to twist these fibers, with the suture "buried" among the fiber. Later the chuck was rotated counterclockwise to ensure that the suture did not coil or snap, while the fiber coating remained intact.

Results

As confirmed using SEM, a uncoated 10-0 nylon suture had a smooth surface and a diameter of approximately 25 µm. The coated 10-0 nylon suture had hundreds of twisted nanofibers covering the surface of the suture in a compacted, spiral manner. With the coating, the overall diameter was increased for about 5 µm.

Example 4: Rotation of Drill Chuck to Form a Hollow Tubular Device Made of Fibers Materials and Methods As shown in FIG. 11, biodegradable polyglycolide (PGA) was dissolved at 10 wt % in hexafluoroisopropanol (HFIP) and loaded into a syringe 120. A 120 W regulated high voltage DC power source 100 was applied to a blunt tip needle 110 on the end of a syringe 120. The electrified polymer solution 130d held in the syringe 120 was pushed at a rate of 450 μL/hr as controlled by a NE-1000 Programmable Single Syringe Pump 140. The collector 204 included a 50 μm-thick wire 490 inserted in a needle 480 that was held by a drill chuck 270 (having a 0⅜" capacity), and the drill chuck was attached to adaptor 260. The adaptor 152b was attached to a 1.21" shaft (shaft unnoticeable from FIG. 11 as it is within the adaptor, but shown in FIG. 12A) on a mounted 120V, ⅓ hp, 300-3,450 rpm speed-control motor 150. A 50 μm-thick wire 490 inserted in a blunt tip needle 480 that was held by a grounded, drill chuck 270 was used as a collector 204, and a standalone, parallel, grounded stand was used as another collector 202 in this example.

When a charged polymer jet was ejected from the needle, it deposited in the air gap between both collectors 204 and 202. As the drill chuck continued to rotate the template wire, hundreds and thousands of fibers coated the template wire. A heat treatment above the glass transition temperature of the polymer was performed to enhance the mechanical properties. In the end, excess length of fibers (between the edge of the template wire and the standalone, parallel stand) was cut out, and the fibers coating the template wire were separated from the wire itself.

Results

As confirmed under the SEM, fibers were compact and they coated the template wire. When the wire was removed, the fibers were in a tube structure.

Figure 13:
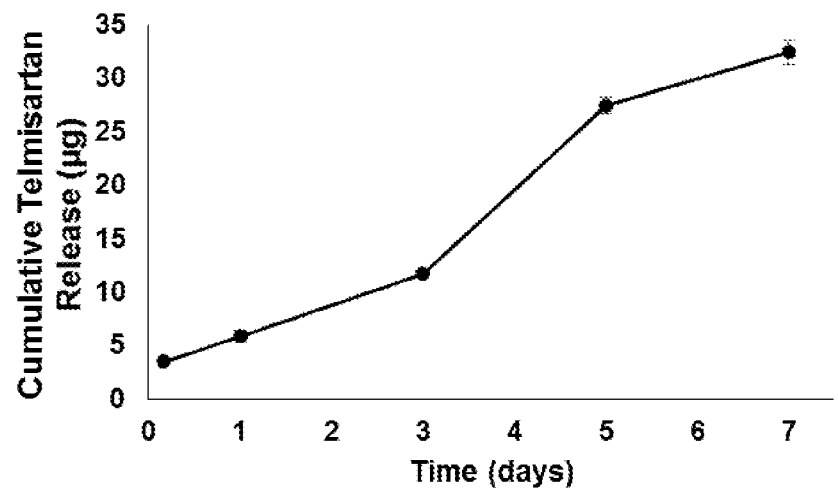
FIG. 13 is a line graph showing the cumulative release of telmisartan (μg) over time (days) from PGA nanofiber-based graft.

A hollow tubular device made from this PGA nanofiber-based mesh was capable to serve as an absorbable, nanostructured vascular graft. Scanning electron microscopy images confirmed an exemplary PGA mesh graft had a lumen diameter of 1.1 mm, an overall device diameter of 1.45 mm (therefore tube wall thickness about 0.175 mm), and a length of about 3 mm. The prepared device using a PGA nanofiber-based graft as a vascular graft exhibited a 150% increase in graft patency when compared to using an unwoven PGA mesh graft. FIG. 13 shows the cumulative release of telmisartan from the PGA nanofiber-based graft. While stenosis (narrowing of the vessel) is a big challenge for synthetic vascular graft and synthetic grafts for bypass of small-diameter (<6 mm) arteries have patency percentage of 40% at 6 months and 25% at 3 years, it was believed that sustained drug delivery from the nanofiber-based mesh/graft could achieve >75% patency of the graft.

Example 5: Multi-Fiber Mesh for Sustained Release of Sunitinib and Inhibition of Choroidal Neovascularization In Vivo Materials & Methods PLGA polymeric nanofiber-based mat or mesh was prepared as described in Example 1. Poly(D,L-lactide-co-glycolide) (PLGA; 50:50; i.v.=0.32-0.44 dl/g) was purchased from Evonik Nutrition & Care GmbH (Germany). Hexafluoroisopropanol (HFIP) was purchased from Sigma Aldrich (St. Louis, Mo.). Sunitinib malate was purchased from LC Laboratories (Woburn, Mass.). Disposable syringes and 1× Dulbecco's Phosphate-Buffered Saline (PBS) were purchased from Fisher Scientific (Waltham, Mass.). 25 G blunt tip needles were purchased from Nordson EFD (East Providence, R.I.). PLGA was dissolved in HFIP at 20% w/w and then electrospun for 120 min at a flow rate of 250 μL/hr through a 25 G blunt tip needle, with an applied voltage of 10.5 kV, and at a distance of 24 cm from a static, grounded collector. PLGA/sunitinib meshes were manufactured under the same conditions at a 10% sunitinib/PLGA concentration (w/w).

Results

Scanning electron microscopy images showed hundreds and thousands of PLGA nanofibers or PLGA nanofibers containing encapsulated sunitinib were deposited, resulting in a mesh. The physical properties of the meshes are shown in Table 1.

TABLE 1

| Nanofiber mesh properties | | | |
| --- | --- | --- | --- |
| Mesh | Thickness (μm) | Water Vapor Flux (g/(h · m$^2$)) | Breaking Strength (N) |
| PLGA | 13 ± 2 | 186 ± 7 | 0.64 ± 0.02 |
| PLGA/Sunitinib | 13 ± 2 | 175 ± 6 | 0.69 ± 0.06 |

Figure 14:
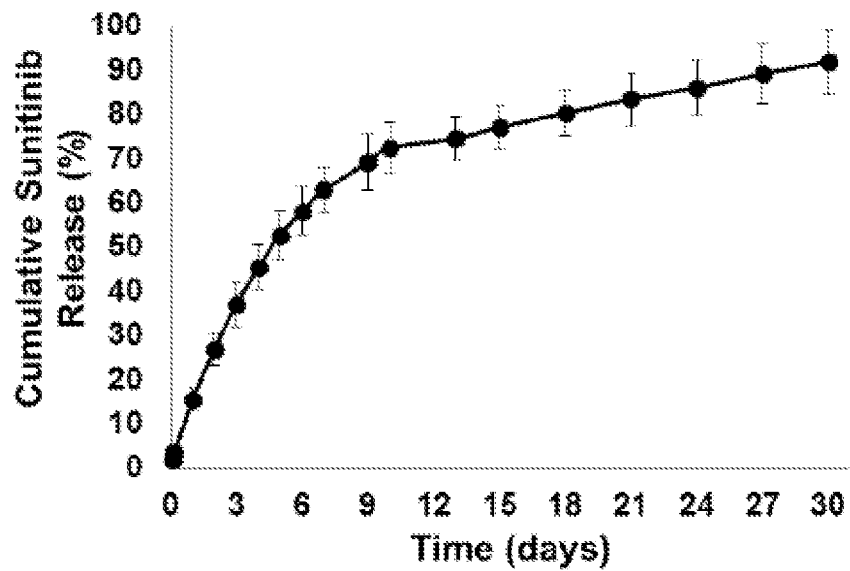
FIG. 14 is a line graph showing the cumulative release of sunitinib (μg) over time (days) from PLGA nanofiber-based mesh.

FIG. 14 shows in vitro sustained release of sunitinib over 30 days. Overall, absorbable, high strength, permeable nanofiber meshes were manufactured capable of sustained sunitinib release.

Figure 15A:
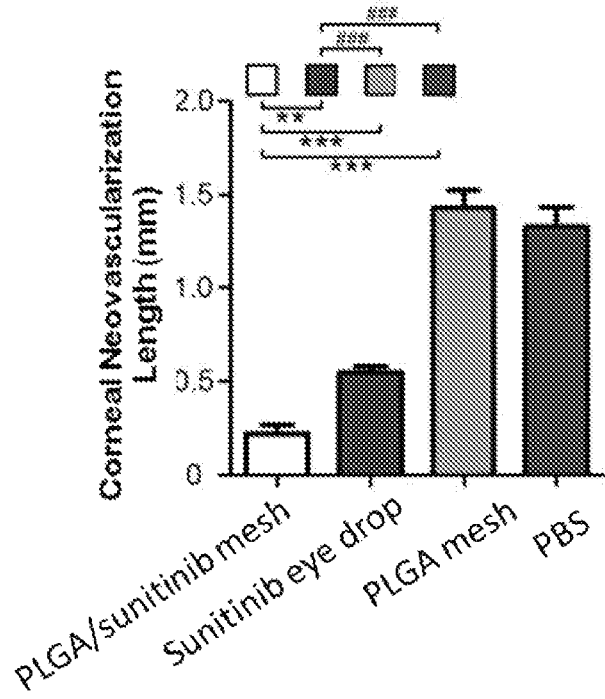
FIGS. 15A and 15B are bar graphs showing the length (mm, FIG. 15A) and the area ($mm^2$, FIG. 15B) of corneal neovascularization in animal eyes when implanted with a PLGA/sunitinib nanofiber-based mesh, topically administered with sunitinib eye drop three times daily, implanted with a PLGA nanofiber-based mesh lacking sunitinib, or topically administered with phosphate buffered saline (PBS).
Figure 15B:
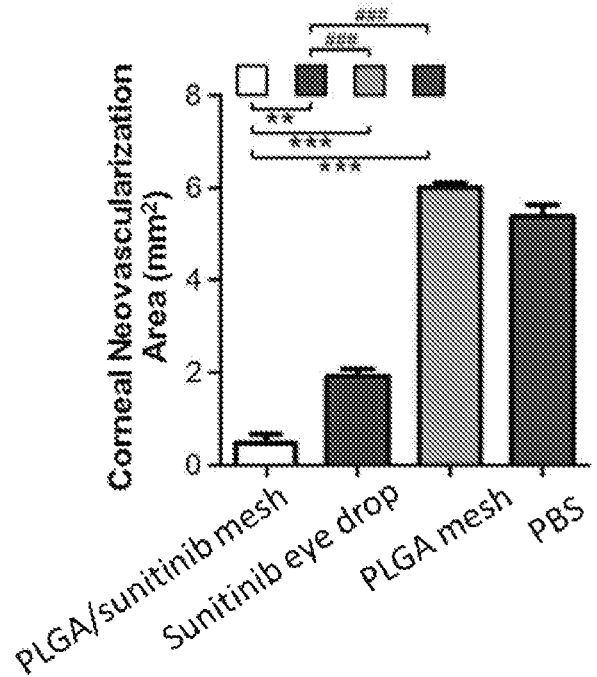

FIGS. 15A and 15B show sunitinib mesh inhibited choroidal neovascularization more significantly than three times daily topical dose of sunitinib. This was confirmed by visual and histological examination of the eyes.

We claim:

1. A method of making aligned twisted fibers, comprising:
    extruding or spraying an electrically charged polymer solution, dispersion, gel, or melt toward one or more grounded collectors to continuously form aligned polymeric fibers comprising aligned polymers,
    wherein at least one of the collectors are rotated to form the aligned polymeric fibers into twisted multifilament threads, sheets, tubes or coatings on tubes.

2. The method of claim 1, wherein the formed polymeric fibers coat the surface of a device connected to the one or more grounded collectors.

3. The method of claim 2, wherein the device comprises one or more threads or sutures.

4. The method of claim 1, wherein the polymeric fibers form a mat, mesh, suture, shunt, scaffold, or graft.

5. The method of claim 1 for making a drug-loaded suture comprising:
    twisting a plurality of polymeric fibers formed by extruding or spraying an electrically charged polymer solution, dispersion, gel, or melt comprising a therapeutic, prophylactic, or diagnostic agent to align the fibers in a system comprising:
    an electrically charged polymer solution, dispersion, gel, or melt, and one or more grounded collectors,
    wherein the electrically charged polymer solution forms aligned polymeric fibers on the one or more grounded collectors, and
    wherein at least one of the collectors can be rotated to twist the polymeric fibers to form a multifilament thread.

6. The method of claim 5, wherein the multifilament thread comprises at least 1 wt % of the therapeutic, prophylactic, or diagnostic agent, and has a greater tensile strength than a non-twisted monofilament polymeric fiber of an identical composition.

7. The method of claim 5, wherein the electrically charged polymer solution, dispersion, gel, or melt comprises between about 8 wt % and about 80 wt % therapeutic, prophylactic, or diagnostic agent compared to the polymer amount.

8. The method of claim 1, wherein the polymer solution is extruded through one or more needles or nozzles to deposit on the one or more grounded collectors to form polymeric fibers.

9. The method of claim 8, wherein at least two grounded collectors are capable of rotation to twist polymeric fibers from both ends.

10. The method of claim 8, wherein the polymeric fibers are nanofibers, micro-fibers, or a combination thereof.

11. The method of claim 1, wherein the one or more grounded collectors comprise a cylindrical drum or rod, and the polymeric fibers form a mesh on the surface of the cylindrical drum.

12. The method of claim 1, wherein the one or more grounded collectors comprise a cylindrical drum or rod, and the polymeric fibers forms aligned fiber arrays.

13. A method of making aligned or twisted fibers, comprising:
    extruding or spraying an electrically charged polymer solution, dispersion, gel, or melt toward one or more grounded collectors to form polymeric fibers,
    wherein the one or more grounded collectors comprise a chuck and a stand-alone collector, and wherein the polymeric fibers have an end on the chuck or an attachment to the chuck capable of rotation and an end on the stand-alone collector.

14. The method of claim 13, wherein the chuck rotates to twist the polymeric fibers in a sufficient degree to increase tensile strength of the twisted polymeric fibers, compared to non-twisted or insufficiently twisted polymeric fibers.

15. The method of claim 1, wherein the one or more grounded collectors comprise a chuck, a stand-alone collector, and a thread between the chuck and the stand-alone collector, and wherein polymeric fibers coat the surface of the thread.

16. The method of claim 15, wherein the thread is connected to a needle to function as a suture.

17. A method of making aligned or twisted fibers, comprising:
    extruding or spraying an electrically charged polymer solution, dispersion, gel, or melt toward one or more grounded collectors to form polymeric fibers,
    wherein at least one of the collectors are rotated to align or twist the polymeric fibers,
    wherein the one or more grounded collectors comprise a chuck, a stand-alone collector, and a template wire at least attached to the chuck, and wherein polymeric fibers forms a tubular device around the surface of the template wire.

18. The method of claim 1, wherein the one or more grounded collectors comprise a device to be coated with polymeric fibers.

19. The method of claim 18, wherein the device to be coated comprises a stent, a catheter, a blade, or a suture.

* * * * *